United States Patent
Collias et al.

(10) Patent No.: US 9,828,325 B2
(45) Date of Patent: Nov. 28, 2017

(54) METHOD FOR THE DEHYDRATION OF LACTATE SALT TO ACRYLIC ACID OR ACRYLIC SALT

(71) Applicant: The Procter & Gamble Company, Cincinnati, OH (US)

(72) Inventors: Dimitris Ioannis Collias, Mason, OH (US); Juan Esteban Velasquez, Cincinnati, OH (US); Jane Ellen Godlewski, Loveland, OH (US); Jeffrey Charles Hayes, West Chester, OH (US); William David Laidig, Hamilton, OH (US)

(73) Assignee: The Procter & Gamble Company, Cincinnati, OH (US)

( * ) Notice: Subject to any disclaimer, the term of this patent is extended or adjusted under 35 U.S.C. 154(b) by 0 days.

(21) Appl. No.: 15/067,210

(22) Filed: Mar. 11, 2016

(65) Prior Publication Data

US 2016/0264507 A1 Sep. 15, 2016

Related U.S. Application Data

(60) Provisional application No. 62/132,538, filed on Mar. 13, 2015.

(51) Int. Cl.
*C07C 51/377* (2006.01)
*C07C 51/41* (2006.01)

(52) U.S. Cl.
CPC ............ *C07C 51/377* (2013.01); *C07C 51/41* (2013.01)

(58) Field of Classification Search
CPC .............................. C07C 51/377; C07C 51/41
See application file for complete search history.

(56) References Cited

U.S. PATENT DOCUMENTS

| | | | | |
|---|---|---|---|---|
| 2,859,240 A * | 11/1958 | Holmen | ................ | C07C 51/377 502/208 |
| 4,729,978 A | 3/1988 | Sawicki | | |
| 2013/0274516 A1* | 10/2013 | Velasquez | ............ | B01J 27/1806 562/599 |
| 2015/0232890 A1* | 8/2015 | Chwae | .................. | C07C 51/377 435/136 |

FOREIGN PATENT DOCUMENTS

WO     WO2014111363 A1     7/2014

OTHER PUBLICATIONS

Zhang, J., et al., Evaluation f Catalysts and optimizatin of reaction conditins for the dehydration of methyl lactate to acrylates, 2008, Chinese Journal of Chemical Engineering, vol. 16, No. 2, pp. 263-269.*
International Search Report and Written Opinion for (PCT/US2016/020663) dated May 20, 2016.
Blanco, E. et al., "Gas phase dehydration of lactic acid to acrylic acid over alkaline-earth phosphates catalysts", Catalysis Today, vol. 226, Dec. 27, 2014, pp. 185-191.
Carl, T., Lira et al; "Conversion of lactic acid to acrylic acid in near-critical water", Industrial & Engineering Chemistry Research, vol. 32, No. 11, pp. 2608-2613.
Reijenga et al., "Development of Methods for the Determination of pKa Values", Analytical Chemistry Insights, vol. 20138, Jan. 1, 2013, pp. 53-71.
Wadley, D.C. et al., "Lactic Acid Conversion to 2,3-Pentanedione and Acrylic Acid Over Silica-Supported Sodium Nitrate: Reaction Optimization and Identification of Sodium Lactate as the Active Cataylst", Journal of Catalysis, vol. 165, No. 2, Jan. 15, 1997, pp. 162-171.

* cited by examiner

*Primary Examiner* — Yate K Cutliff
(74) *Attorney, Agent, or Firm* — Brent M. Peebles

(57) ABSTRACT

Methods for catalytically dehydrating lactate salt to acrylic acid, acrylate salt, or mixtures thereof with high yield and selectivity and without significant conversion to undesired side products, such as, acetaldehyde, propionic acid, and acetic acid, are provided. The catalysts include acid-base bifunctional catalysts.

17 Claims, No Drawings

METHOD FOR THE DEHYDRATION OF LACTATE SALT TO ACRYLIC ACID OR ACRYLIC SALT

FIELD OF THE INVENTION

The present invention generally relates to methods of catalytic conversion of lactate salt to acrylic acid, acrylate salt, or mixtures thereof. More specifically, the invention relates to methods of using catalysts useful for the dehydration of lactate salt to acrylic acid, acrylate salt, or mixtures thereof with high yield and selectivity to acrylic acid, acrylate salt, or mixtures thereof, short residence time, and without significant conversion of the lactate salt to undesired side products, such as, for example, acetaldehyde, propionic acid, acetic acid, 2,3-pentanedione, carbon dioxide, and carbon monoxide. The catalysts include acid-base bifunctional catalysts which have an acidic site and a basic site, wherein the acidic site is a Brønsted acid with a $pK_a$ of about 4 to about 7, or has a Hammett acidity function $H_0$ of about 4 to about 7.

BACKGROUND OF THE INVENTION

Acrylic acid, acrylic acid derivatives, or mixtures thereof have a variety of industrial uses, typically consumed in the form of polymers. In turn, these polymers are commonly used in the manufacture of, among other things, adhesives, binders, coatings, paints, polishes, detergents, flocculants, dispersants, thixotropic agents, sequestrants, and superabsorbent polymers, which are used in disposable absorbent articles, including diapers and hygienic products, for example. Acrylic acid is commonly made from petroleum sources. For example, acrylic acid has long been prepared by catalytic oxidation of propylene. These and other methods of making acrylic acid from petroleum sources are described in the Kirk-Othmer Encyclopedia of Chemical Technology, Vol. 1, pgs. 342-369 ($5^{th}$ Ed., John Wiley & Sons, Inc., 2004). Petroleum-based acrylic acid contributes to greenhouse emissions due to its high petroleum derived carbon content. Furthermore, petroleum is a non-renewable material, as it takes hundreds of thousands of years to form naturally and only a short time to consume. As petrochemical resources become increasingly scarce, more expensive, and subject to regulations for $CO_2$ emissions, there exists a growing need for bio-based acrylic acid, acrylic acid derivatives, or mixtures thereof that can serve as an alternative to petroleum-based acrylic acid, acrylic acid derivatives, or mixtures thereof.

Many attempts have been made over the last 40 to 50 years to make bio-based acrylic acid, acrylic acid derivatives, or mixtures thereof from non-petroleum sources, such as lactic acid (also known as 2-hydroxypropionic acid), 3-hydroxypropionic acid, glycerin, carbon monoxide and ethylene oxide, carbon dioxide and ethylene, and crotonic acid. From these non-petroleum sources, only lactic acid is produced today in high yield from sugar (≥90% of theoretical yield, or equivalently, ≥0.9 g of lactic acid per g of sugar) and purity, and economics which could support producing acrylic acid at a cost competitive to petroleum-based acrylic acid. As such, lactic acid or lactates present a real opportunity of serving as feedstocks for bio-based acrylic acid, acrylic acid derivatives, or mixtures thereof. Also, 3-hydroxypropionic acid is expected to be produced at commercial scale in a few years, and as such, 3-hydropropionic acid will present another real opportunity of serving as feedstock for bio-based acrylic acid, acrylic acid derivatives, or mixtures thereof. Sulfate salts; phosphate salts; mixtures of sulfate and phosphate salts; bases; zeolites or modified zeolites; metal oxides or modified metal oxides; and supercritical water are the main catalysts which have been used to dehydrate lactic acid or lactate to acrylic acid, acrylic acid derivatives, or mixtures thereof in the past with varying success.

For example, U.S. Pat. No. 4,786,756 (issued in 1988), describes the vapor phase dehydration of lactic acid or ammonium lactate to acrylic acid using aluminum phosphate ($AlPO_4$) treated with an aqueous inorganic base as a catalyst. As an example, the '756 patent discloses a maximum yield of acrylic acid of 43.3% when lactic acid was fed into the reactor at approximately atmospheric pressure, and a respective yield of 61.1% when ammonium lactate was fed into the reactor. In both examples, acetaldehyde was produced at yields of 34.7% and 11.9%, respectively, and other side products were also present in large quantities, such as, propionic acid, CO, and $CO_2$. Omission of the base treatment caused increased amounts of the side products. Another example is Hong et al. (2011) *Appl. Catal. A: General* 396:194-200, who developed and tested composite catalysts made with $Ca_3(PO_4)_2$ and $Ca_2(P_2O_7)$ salts with a slurry-mixing method. The catalyst with the highest yield of acrylic acid from methyl lactate was the 50%-50% (by weight) catalyst. It yielded 68% acrylic acid, about 5% methyl acrylate, and about 14% acetaldehyde at 390° C. The same catalyst achieved 54% yield of acrylic acid, 14% yield of acetaldehyde, and 14% yield of propionic acid from lactic acid.

Prof. D. Miller's group at Michigan State University (MSU) published many papers on the dehydration of lactic acid or lactic acid esters to acrylic acid and 2,3-pentanedione, such as, Gunter et al. (1994) *J. Catalysis* 148:252-260; and Tam et al. (1999) *Ind. Eng. Chem. Res.* 38:3873-3877. The best acrylic acid yields reported by the group were about 33% when lactic acid was dehydrated at 350° C. over low surface area and pore volume silica impregnated with NaOH. In the same experiment, the acetaldehyde yield was 14.7% and the propionic acid yield was 4.1%. Examples of other catalysts tested by the group were $Na_2SO_4$, NaCl, $Na_3PO_4$, $NaNO_3$, $Na_2SiO_3$, $Na_4P_2O_7$, $NaH_2PO_4$, $Na_2HPO_4$, $Na_2HAsO_4$, $NaC_3H_5O_3$, NaOH, CsCl, $Cs_2SO_4$, KOH, CsOH, and LiOH. In all cases, the above referenced catalysts were tested as individual components, not in mixtures. Finally, the group suggested that the yield to acrylic acid is improved and the yield to the side products is suppressed when the surface area of the silica support is low, reaction temperature is high, reaction pressure is low, and residence time of the reactants in the catalyst bed is short.

Finally, the Chinese patent application 200910054519.7 discloses the use of ZSM-5 molecular sieves modified with aqueous alkali (such as, $NH_3$, NaOH, and $Na_2CO_3$) or a phosphoric acid salt (such as, $NaH_2PO_4$, $Na_2HPO_4$, $LiH_2PO_4$, $LaPO_4$, etc.). The best yield of acrylic acid achieved in the dehydration of lactic acid was 83.9%, however that yield came at very long residence times.

Therefore, the manufacture of acrylic acid, acrylate, or mixtures thereof from lactic acid or lactate by processes, such as those described in the literature noted above, has demonstrated: 1) yields of acrylic acid, acrylate, or mixtures thereof not exceeding 70%; 2) low selectivities of acrylic acid, acrylate, or mixtures thereof, i.e., significant amounts of undesired side products, such as, acetaldehyde, 2,3-pentanedione, propionic acid, CO, and $CO_2$; 3) long residence times in the catalyst beds; and 4) catalyst deactivation in short time on stream (TOS). The side products can deposit onto the catalyst resulting in fouling, and premature and rapid deactivation of the catalyst. Further, once deposited, these side products can catalyze other undesired reactions, such as polymerization reactions. Aside from depositing on the catalysts, these side products, even when present in only small amounts, impose additional costs in processing acrylic acid (when present in the reaction product effluent) in the manufacture of superabsorbent polymers (SAP), for example. These deficiencies of the prior art processes and catalysts render them commercially non-viable.

Accordingly, there is a need for catalysts and methods for the dehydration of lactate salt to acrylic acid, acrylate salt, or mixtures thereof, with high yield, selectivity, and efficiency (i.e., short residence time), and high longevity catalysts.

SUMMARY OF THE INVENTION

A method of making acrylic acid, metal acrylate, or mixtures thereof is provided. In one embodiment of the present invention, the method includes dehydrating a metal lactate by contacting a stream comprising the metal lactate with an acid-base bifunctional catalyst comprising an acidic site and a basic site, and wherein the acidic site is a Brønsted acid with a $pK_a$ of about 4 to about 7. In another embodiment of the present invention, the method includes dehydrating a metal lactate by contacting a stream comprising the metal lactate with an acid-base bifunctional catalyst comprising an acidic site and a basic site, and wherein the acidic site has a Hammett acidity function $H_0$ of about 4 to 7.

A method of making acrylic acid, sodium acrylate, or mixtures thereof is provided. In one embodiment of the present invention, the method includes contacting: (a) a stream comprising: sodium lactate, and a solvent, with (b) an acid-base bifunctional catalyst comprising an acidic site and a basic site, wherein the acidic site is a Brønsted acid with a $pK_a$ of about 4.5 to about 6.2, and wherein the contacting of the stream with the acid-base bifunctional catalyst is performed at a temperature about 250° C. to about 450° C., and at a residence time less than about 1 day, whereby acrylic acid, sodium acrylate, or mixtures thereof are produced as a result of the stream contacting the acid-base bifunctional catalyst.

Additional features of the invention may become apparent to those skilled in the art from a review of the following detailed description, taken in conjunction with the examples.

DETAILED DESCRIPTION OF THE INVENTION

I Definitions

As used herein, the term "acid-base bifunctional catalyst" refers to a catalyst with at least an acidic site and a basic site.

As used herein, the term "Brønsted acid" refers to a material that donates a proton ($H^+$), as it is known to those skilled in the art.

As used herein, the term "Brønsted base" refers to a material that accepts a proton ($H^+$), as it is known to those skilled in the art.

As used herein, the term "Lewis acid" refers to a material that accepts an electron pair, as it is known to those skilled in the art.

As used herein, the term "solid acid" generally refers to a solid on which the color of a basic indicator changes or a solid on which a base is chemically adsorbed, as it is well known to those skilled in the art. As heterogeneous catalysts, solid acids do not dissolve in the reaction medium. Well known examples include zeolites, alumina, and various other metal oxides.

As used herein, the term "$pK_a$" refers to the negative logarithm of the acid dissociation constant, $K_a$, measured in water, at 25° C., and in dilute conditions, as it is well known to those skilled in the art. For the purposes of the present invention, $pK_a$ refers to measurements in water, at 25° C., and in dilute conditions, unless otherwise specified.

As used herein, the term "Hammett acidity function $H_0$" is a measure of acidity of acids in concentrated solutions or solid acids based on indicators. In case the acidic site is a Brønsted acid, $H_0$ is defined as: $H_0=pK_a+\log([B]/[BH^+])$, where B is the base indicator and $BH^+$ is the conjugate acid of the indicator, as it is well known to those skilled in the art. In case the acidic site is a Lewis acid, $H_o$ is defined as: $H_0=pK_a+\log([B]/[AB])$, where B is the base indicator and A is the Lewis acid or electron pair acceptor, as it is well known to those skilled in the art. More information on the Hammett acidity function $H_0$ can be found in Hammett and Deyrup (1932) *JACS* 54:2721-2739, which is incorporated herein by reference. For the purpose of the present invention, the Hammett acidity function $H_0$ is measured in water, at 25° C., and in dilute conditions, unless otherwise specified.

As used herein, the term "monophosphate" refers to any salt whose anionic entity, $[PO_4]^{3-}$, is composed of four oxygen atoms arranged in an almost regular tetrahedral array about a central phosphorus atom.

As used herein, the term "polyphosphate" refers to any salts containing one or several linear P—O—P linkages generated by corner sharing of $[PO_4]^{3-}$ tetrahedra leading to the formation of finite chains.

As used herein, the term "particle span" refers to a statistical representation of a given particle sample and is equal to $(D_{v,0.09}-D_{v,0.10})/D_{v,0.50}$. The term "median particle size" or $D_{v,0.50}$ refers to the diameter of a particle below which 50% of the total volume of particles lies. Further, $D_{v,0.10}$ refers to the particle size that separates the particle sample at the 10% by volume fraction and $D_{v,0.09}$, is the particle size that separates the particle sample at the 90% by volume fraction.

As used herein, the term "conversion" is defined as: {[lactate salt flow rate in (mol/min)−lactate salt flow rate out (mol/min)]/[lactate salt flow rate in (mol/min)]}*100. Equivalently, "conversion" is defined as: [all products flow rate out (mol/min)]/lactate salt flow rate in (mol/min)]*100, and measured in mol %.

As used herein, the term "yield" is defined as: [flow rate out of acrylic acid, metal acrylate, or mixtures thereof (mol/min)/lactate salt flow rate in (mol/min)]*100, and measured in mol %.

As used herein, the term "selectivity" is defined as: {flow rate out of acrylic acid, metal acrylate, or mixtures thereof (mol/min)/[lactate salt flow rate in (mol/min)−lactate salt flow rate out (mol/min)]}*100, and measured in mol %. Equivalently, "selectivity" is defined as: [flow rate out of acrylic acid, metal acrylate, or mixtures thereof (mol/min)/ all products flow rate out (mol/min)]*100, or as: [Yield/ Conversion]*100.

II Catalysts and Catalyst Preparation Methods

Unexpectedly, it has been found that acid-base bifunctional catalysts that have acidic sites with Brønsted acidity and $pK_a$ of about the $pK_a$ of lactic acid to about the $pK_a$ of $KH_2PO_4$ in the reaction (contact) conditions dehydrate lactate salt to acrylic acid, acrylate salt, or mixtures thereof with high: 1) yield and selectivity for acrylic acid, acrylate salt, or mixtures thereof, i.e., low amount and few side products; 2) efficiency, i.e., performance in short residence time; and 3) longevity. Although not wishing to be bound by any theory, applicants believe that the Brønsted acidity of acidic sites in the acid-base bifunctional catalysts should be within a range, i.e., weak enough not to re-protonate the lactate salt, and yet strong enough to dehydrate the lactate salt. Re-protonation of the lactate salt will result in the formation of lactic acid, which itself cannot be, efficiently and with high yield and selectivity, dehydrated to acrylic acid, since the —COOH group of the lactic acid will produce many by-products during the dehydration. Thus, for aqueous solutions of lactate salt, the acidity of the Brønsted acidity of the acidic sites of the acid-base bifunctional catalysts should range from about the acidity of lactic acid ($pK_a \sim 3.9$) to the upper limit of acidity required for the dehydration, which corresponds to a $pK_a \sim 7.2$ (which is the $pK_a$ of $KH_2PO_4$). Obviously, if the solvent or diluent is other than water, the $pK_a$ range described above might shift either direction, but the inventors believe that the main principles described above will remain valid, namely that efficient dehydration will occur when using acid-base bifunctional catalysts with Brønsted acidity of the acidic sites and a $pK_a$ of about the $pK_a$ of lactic acid to about the $pK_a$ of $KH_2PO_4$ in the reaction (contact) conditions.

Unexpectedly, it has also been found that acid-base bifunctional catalysts that have acidic sites with Hammett acidity function $H_0$ of about 4 to about 7 in the reaction (contact) conditions are able to dehydrate lactate salt to acrylic acid, acrylate salt, or mixtures thereof with high: 1) yield and selectivity for acrylic acid, acrylate salt, or mixtures thereof, i.e., low amount and few side products; 2) efficiency, i.e., performance in short residence time; and 3) longevity. Although not wishing to be bound by any theory, applicants believe that the Hammett acidity function $H_0$ of acidic sites in the acid-base bifunctional catalysts should be within a range, i.e., weak enough not to re-protonate the lactate salt, and strong enough to dehydrate the lactate salt. Re-protonation of the lactate salt will result in the formation of lactic acid, which itself cannot be, efficiently and with high yield and selectivity, dehydrated to acrylic acid, acrylate salt, or mixtures thereof, since the —COOH group of the lactic acid will produce many by-products during the dehydration, i.e., not higher than about 7 to be able to perform the dehydration and not lower than about 4 to avoid re-protonating the lactate salt.

The acid-base bifunctional catalyst of the present invention comprises an acidic site and a basic site. In one embodiment, the acidic site of the acid-base bifunctional catalyst is a Brønsted acid characterized by a $pK_a$. In another embodiment, the acidic site of the acid-base bifunctional catalyst is characterized by a Hammett acidity function $H_0$.

Non-limiting examples of acid-base bifunctional catalysts are phosphate, condensed phosphate, phosphate adduct, arsenate, condensed arsenate, nitrate, sulfate, borate, carbonate, chromate, vanadate, niobate, tantalate, selenate, and heteropolyanion, other monomeric oxoanion or polyoxoanion that may be apparent to those having ordinary skill in the art. Non-limiting examples of a heteropolyanion are heteropolyphosphate, such as arsenatophosphate, phosphoaluminate, phosphoborate, phosphochromate, phosphomolybdate, phosphosilicate, phosphosulfate, phosphotungstate, and others that may be apparent to those having ordinary skill in the art. Non-limiting examples of phosphate adducts are adducts of phosphate anions with telluric acid, halides, borates, carbonates, nitrates, sulfates, chromates, silicates, oxalates, mixtures thereof, or others that may be apparent to those having ordinary skill in the art.

In one embodiment, the $pK_a$ of the Brønsted acid of the acidic site of the acid-base bifunctional catalyst is in the range between about the $pK_a$ of lactic acid and about the $pK_a$ of $KH_2PO_4$ in the reaction conditions. At room temperature and in dilute aqueous solutions, lactic acid has a $pK_a$ of about 3.9 and $KH_2PO_4$ has a $pK_a$ of about 7.2. Non-limiting examples of acid-base bifunctional catalysts comprising an acidic site and a basic site, wherein the acidic site is a Brønsted acid with $pK_a$ of about 3.9 to about 7.2 are: dihydrogen phosphate ($H_2PO_4$), ascorbic acid, benzoic acid, carboxyformate ($HC_2O_4$), hydrazoic acid, mono- and di-hydrogen citrate ($H_2C_6H_5O_7^-$ and $HC_6H_5O_7^{2-}$), acetic acid, propionic acid, pyridinium ion ($C_5H_4NH^+$), carbonic acid ($H_2CO_3$), hydrogen sulfite ($HSO_3^-$), dihydrogen arsenate ($H_2AsO_4^-$), hydrogen sulfate ($HSO_4^-$), crotonic acid, homogentisic acid, maleic acid, malic acid, protocatechuic acid, tartaric acid, telluric acid, periodic acid, mono-hydrogen chromate ($HCrO_4^-$), butyric acid, ascorbic acid, and vinylacetic acid.

For the purpose of the present invention, a distance between the acidic site and the basic site of an acid-base bifunctional catalyst is understood to mean: 1) the distance between the centroid of the electron-pair accepting element and the centroid of the proton-accepting element in a Lewis acid/Brønsted base bifunctional catalyst, or 2) the distance between the centroid of the proton-donating element and the centroid of the proton-accepting element in a Brønsted acid/Brønsted base bifunctional catalyst. For example, acetic acid is a Brønsted acid/Brønsted base bifunctional catalyst wherein a proton is donated from the OH entity of the carboxylic acid group (CO(OH)) and a proton is accepted onto the oxygen of the carbonyl entity (C=O) in the carboxylic acid group (CO(OH)); and the distance between the acidic site and the basic site is the distance between the oxygen atom of the OH entity and the oxygen atom of the carbonyl entity.

At room temperature and in solvents other than water, the $pK_a$ values of Brønsted acids are affected by the protic nature of the solvent (i.e., ability to form hydrogen bonds), and its donor number (a solvent with high donor number has strong ability to donate an electron pair) and dielectric constant (relative permittivity; a solvent with high dielectric constant (i.e., high polarity) is a good solvent for ionic species). However, the relative ranking of Brønsted acids by $pK_a$ is expected to remain essentially the same in various solvents or mixed solvent systems. For example, the approximate $pK_a$ values of acetic acid in water, dimethylsulfoxide (DMSO), and acetonitrile (ACN) are 4.8, 12.6, and 23.5. The respective approximate $pK_a$ values for benzoic acid are 4.2, 11.1, and 21.5, and for 2,4-dinitrophenol are 3.9, 5.1, and 16.7.

Similarly, temperature affects the $pK_a$ value of Brønsted acids according to the van't Hoff equation $d\ln K_a/dT = \Delta H/RT^2$, where $\Delta H$ is the enthalpy change, and R is the universal gas constant. In some cases, the dissociation of Brønsted acids is an endothermic process, increasing the temperature in the system will result in the production of a higher number of protons, which increases the $K_a$ and decreases the $pK_a$. However, the relative ranking of Brønsted acids by $pK_a$ is expected to remain the same at higher temperatures for some catalysts.

In one embodiment, the acid-base bifunctional catalyst comprises an acidic site and a basic site, wherein the acidic site is a Brønsted acid with a p$K_a$ of about 3.9 to about 7.2. In another embodiment, the acid-base bifunctional catalyst comprises an acidic site and a basic site, wherein the acidic site is a Brønsted acid with a p$K_a$ of about 4 to about 7. In yet another embodiment, the acid-base bifunctional catalyst comprises an acidic site and a basic site, wherein the acidic site is a Brønsted acid with a p$K_a$ of about 4.5 to about 6.2. In one embodiment, the acid-base bifunctional catalyst comprises an acidic site and a basic site, wherein the acidic site is a Brønsted acid with a p$K_a$ of about 5.3.

In one embodiment, the acid-base bifunctional catalyst consists essentially of a diprotonated monophosphate. In another embodiment, the acid-base bifunctional catalyst consists essentially of a phosphate anion described by the formula $[H_{2(1-v)}PO_{4-v}]^{nv-}{}_{nv}$, wherein n is any integer equal to or greater than 2 and v is greater than or equal to zero and less than 1.

In some embodiments, the acid-base bifunctional catalyst contains one or more cations. The cation of the basic site of an acid-base bifunctional catalyst of the present invention can be monovalent or polyvalent. Non-limiting examples of monovalent cations are $Li^+$, $Na^+$, $K^+$, $Rb^+$, $Cs^+$, $Ag^+$, $Rb^+$, $Tl^+$, and mixtures thereof. In one embodiment, the monovalent cation is selected from the group consisting of $Li^+$, $Na^+$, $K^+$, $Rb^+$, $Cs^+$, and mixtures thereof. In another embodiment, the monovalent cation is $Na^+$ or $K^+$; and in yet another embodiment, the monovalent cation is $K^+$. In one embodiment, the diprotonated monophosphate is selected from the group consisting of $LiH_2PO_4$, $NaH_2PO_4$, $KH_2PO_4$, $RbH_2PO_4$, $CsH_2PO_4$, and mixtures thereof. In another embodiment, the diprotonated monophosphate is selected from the group consisting of $KH_2PO_4$, $RbH_2PO_4$, $CsH_2PO_4$, and mixtures thereof.

In one embodiment, the polyvalent cation of the basic site of an acid-base bifunctional catalyst of the present invention is selected from the group consisting of divalent cations, trivalent cations, tetravalent cations, pentavalent cations, and mixtures thereof. Non-limiting examples of polyvalent cations are cations of the alkaline earth metals (i.e., Be, Mg, Ca, Sr, Ba, and Ra), transition metals (e.g. Y, Ti, Zr, V, Nb, Cr, Mo, Mn, Re, Fe, Ru, Co, Rh, Ni, Pd, Pt, Cu, Ag, and Au), poor metals (e.g. Zn, Ga, Si, Ge, B, Al, In, Sb, Sn, Bi, and Pb), lanthanides (e.g. La and Ce), and actinides (e.g. Ac and Th). In one embodiment, the polyvalent cation is selected from the group consisting of $Be^{2+}$, $Mg^{2+}$, $Ca^{2+}$, $Sr^{2+}$, $Ba^{2+}$, $Mn^{2+}$, $Fe^{2+}$, $Co^{2+}$, $Ni^{2+}$, $Cu^{2+}$, $Zn^{2+}$, $Cd^{2+}$, $Sn^{2+}$, $Pb^{2+}$, $Ti^{3+}$, $Cr^{3+}$, $Mn^{3+}$, $Fe^{3+}$, $Al^{3+}$, $Ga^{3+}$, $Y^{3+}$, $In^{3+}$, $Sb^{3+}$, $Bi^{3+}$, $Si^{4+}$, $Ti^{4+}$, $V^{4+}$, $Ge^{4+}$, $Mo^{4+}$, $Pt^{4+}$, $V^{5+}$, $Nb^{5+}$, $Sb^{5+}$, and mixtures thereof. In another embodiment, the polyvalent cation is selected from the group consisting of $Ca^{2+}$, $Ba^{2+}$, $Cu^{2+}$, $Mn^{2+}$, $Mn^{3+}$, and mixtures thereof; in yet another embodiment, the polyvalent cation is selected from the group consisting of $Ca^{2+}$, $Ba^{2+}$, $Mn^{2+}$, and mixtures thereof; and in even yet another embodiment, the polyvalent cation is $Ba^{2+}$.

In one embodiment, the acid-base bifunctional catalyst is generated from a polyphosphate by hydrolysis. In another embodiment, the polyphosphate is selected from the group consisting of $Li_2H_2P_2O_7$, $Li_3H_2P_3O_{10}$, $Li_4H_2P_4O_{13}$, $Li_3P_3O_9$, $Li_4P_4O_{12}$, $Li_6P_6O_{18}$, $Li_8P_8O_{24}$, $Li_{10}P_{10}O_{30}$, $(LiPO_3)_n$, $Na_2H_2P_2O_7$, $Na_3H_2P_3O_{10}$, $Na_4H_2P_4O_{13}$, $Na_3P_3O_9$, $Na_4P_4O_{12}$, $Na_6P_6O_{18}$, $Na_8P_8O_{24}$, $Na_{10}P_{10}O_{30}$, $(NaPO_3)_n$, $K_2H_2P_2O_7$, $K_3H_2P_3O_{10}$, $K^H{}_2P_4O_{13}$, $K_3{}^P{}_3O_9$, $K_4P_4O_{12}$, $K_6P_6O_{18}$, $K_8P_8$, $O_{24}$, $K_{10}P_{10}O_{30}$, $(KPO_3)_n$, $Rb_2H_2P_2O_7$, $Rb_3H_2P_3O_{10}$, $Rb_4H_2P_4O_{13}$, $Rb_3P_3O_9$, $Rb_4{}^P{}_4O_{12}$, $Rb_6P_6O_{18}$, $Rb_8P_8O_{24}$, $Rb_{10}P_{10}O_{30}$, $(RbPO_3)_n$, $Cs_2H_2P_2O_7$, $Cs_3H_2P_3O_{10}$, $Cs_4H_2P_4O_{13}$, $Cs_3P_3O_9$, $Cs_4P_4O_{12}$, $Cs_6P_6O_{18}$, $Cs_8P_8O_{24}$, $Cs_{10}P_{10}O_{30}$, $(CsPO_3)_n$, and mixtures thereof. Hydrolysis of these polyphosphates generates the respective diprotonated monophosphates $LiH_2PO_4$, $NaH_2PO_4$, $KH_2PO_4$, $RbH_2PO_4$, $CsH_2PO_4$, and mixtures thereof. This hydrolysis can take place either before or during the reaction of making acrylic acid, acrylate salt, or mixtures thereof.

In one embodiment, the catalyst is a solid acid. Non-limiting examples of solid acids are clay minerals; acids adsorbed onto silica, quartz, alumina, and diatomaceous earth; cation exchange resins; inorganic chemicals; and mixed oxides. Non-limiting examples of clay minerals are bentonite, kaolinite, montmorillonite, and zeolites. Non-limiting examples of adsorbed acids are sulfuric acid and phosphoric acid. Non-limiting examples of inorganic chemicals are $ZnO$, $Al_2O_3$, $TiO_2$, $CeO_2$, $CaSO_4$, $AlCl_3$, and $BaSO_4$. Non-limiting examples of mixed oxides are $SiO_2.Al_2O_3$, $ZrO_2.SiO_2$, $MgO.SiO_2$, and $TiO_2.ZnO$.

In one embodiment, the acid-base bifunctional catalyst comprises an acidic site and a basic site, wherein the acidic site has a Hammett acidity function $H_0$ of about 4 to about 7. In another embodiment, the acid-base bifunctional catalyst comprises an acidic site and a basic site, wherein the acidic site has a Hammett acidity function $H_0$ of about 5 to about 6.

In one embodiment, the acid-base bifunctional catalyst comprises acidic sites and basic sites, wherein some acidic sites are Brønsted acids and some acidic sites are Lewis acids. Non-limiting examples of these acid-base bifunctional catalysts are $KH_2PO_4$ and $ZrO_2$, $NaHSO_4$ and $Al_2O_3.SiO_2$; and $Te(OH)_6$ and $SiO_2$.

In one embodiment, the acid-base bifunctional catalyst comprises an acidic site and a basic site, wherein the distance between the acidic site and the basic site is about 2.4 Å to about 3 Å. In another embodiment, the acid-base bifunctional catalyst comprises an acidic site and a basic site, wherein the distance between the acidic site and the basic site is about 2.5 Å to about 2.8 Å. In yet another embodiment, the acid-base bifunctional catalyst comprises an acidic site and a basic site, wherein the distance between the acidic site and the basic site is about 2.6 Å.

The spacing between the oxygen in the —OH group and the proton in the $CH_3$ group in the lactic acid, that have to be eliminated for the dehydration reaction to occur, is estimated to be 2.66 Å (the estimation was done using Jmol—an open-source Java viewer for chemical structures in 3D; http://www.jmol.org/). Similar spacing between the oxygen in the —OH group and the proton in the $CH_3$- or $CH_2$-groups that have to be eliminated for the dehydration reaction to occur is found in alcohols, e.g. 2.66 Å for ethanol and 2-propanol, and 2.67 Å for 1-butanol. For comparison, the carbon-carbon spacing in the lactic acid or alcohols is about 1.53 Å. Non-limiting examples of acid-base bifunctional catalysts that have spacing between the acidic and basic sites between about 2.4 Å and about 3 Å are: sulfurous acid 2.3 Å; sulfuric acid, salts of hydrogen sulfate, sulfurous acid, and bisulfite salts 2.36 Å; perchloric acid 2.44 Å; phosphoric acid, phosphorous acid, pyrophosphoric acid, salts of hydrogen pyrophosphate, salts of dihydrogen pyrophosphate, and salts of hydrogen phosphite 2.52 Å; salts of dihydrogen phosphate 2.58 Å; selenous acid 2.6 Å; perrhenic acid 2.65 Å; chromic acid and salts of hydrogen chromate 2.72 Å; selenic acid and salts of hydrogen selenate 2.75 Å; pyruvic acid 2.77 Å; arsenic acid and salts of dihydrogen arsenate 2.8 Å; xenic acid 2.83 Å; telluric acid 2.87 Å; ascorbic acid 2.95 Å; molybdic acid 3.06 Å; and tungstic acid 3.08 Å.

The acid-base bifunctional catalyst can include an inert support that is constructed of a material selected from the group consisting of silicates, aluminates, zirconates, carbons, metal oxides, and mixtures thereof. Alternatively, the support is inert relative to the reaction mixture expected to contact the catalyst. In the context of the reactions expressly described herein, in one embodiment the support is a low surface area silica or zirconia. When present, the support represents an amount of about 5 wt % to about 98 wt %, based on the total weight of the catalyst. Generally, a catalyst that includes an inert support can be made by one of two exemplary methods: impregnation or co-precipitation. In the impregnation method, a suspension of the solid inert support is treated with a solution of a pre-catalyst, and the resulting material is then activated under conditions that will convert the pre-catalyst to a more active state. In the co-precipitation method, a homogenous solution of the catalyst ingredients is precipitated by the addition of additional ingredients.

In one embodiment of the invention, the acid-base bifunctional catalyst is calcined. Calcination is a process that allows chemical reaction, and/or thermal decomposition, and/or phase transition, and/or removal of volatile materials. The calcination process is carried out with any equipment known to those skilled in the art, such as, by way of example and not limitation, furnaces or reactors of various designs, including shaft furnaces, rotary kilns, hearth furnaces, and fluidized bed reactors. The calcination temperature is, in one embodiment of the present invention, about 200° C. to about 1200° C. In another embodiment of the present invention, the calcination temperature is about 250° C. to about 900° C. In yet another embodiment of the present invention, the calcination temperature is about 300° C. to about 600° C. The calcination time is, in one embodiment of the present invention, about one hour to about seventy-two hours.

While many methods and machines are known to those skilled in the art for fractionating particles into discreet sizes and determining particle size distribution, sieving is one of the easiest, least expensive, and common ways. An alternative way to determine the size distribution of particles is with light scattering. Following calcination, the acid-base bifunctional catalyst is, in one embodiment of the present invention, ground and sieved to provide a more uniform product. The particle size distribution of the acid-base bifunctional catalyst particles includes a particle span that, in one embodiment of the present invention, is less than about 3; in another embodiment of the present invention, the particle size distribution of the catalyst particles includes a particle span that is less than about 2; and in yet another embodiment of the present invention, the particle size distribution of the catalyst particles includes a particle span that is less than about 1.5. In another embodiment of the present invention, the acid-base bifunctional catalyst is sieved to a median particle size of about 50 μm to about 500 μm. In yet another embodiment of the present invention, the acid-base bifunctional catalyst is sieved to a median particle size of about 100 μm to about 200 μm.

In one embodiment of the present invention, the method of preparing the acid-base bifunctional catalyst includes molding the catalyst particles. Non-limiting examples of molding operations are granulation, agglomeration, compaction, pelleting, and extrusion.

The acid-base bifunctional catalyst of the present invention can be utilized to catalyze several chemical reactions. Non-limiting examples of reactions are: dehydration of metal hydroxypropionate, oxydehydration of glycerin to acrolein, dehydration of aliphatic alcohols to alkenes or olefins, dehydration of ethanolamine to ethylenimine, dehydrogenation of aliphatic alcohols to ethers, dehydration of bicyclic ethers produced by the Diels-Alder reaction of a furan molecule with ethylene (e.g. 2,5-dimethylfuran (DMF) and ethylene produces 1,4-dimethyl-7-oxa-bicyclo[2,2,1]-hept-2-ene or 2,5-furandicarboxylic acid (FDCA) and ethylene produces 7-oxa-bicyclo[2.2.1]-hept-2-ene-1,4-dicarboxylic acid to produce substituted aromatics, e.g. para-xylene or terephthalic acid), other dehydrogenations, hydrolyses, alkylations, dealkylations, oxidations, disproportionations, esterifications, cyclizations, isomerizations, condensations, aromatizations, polymerizations, and other reactions that may be apparent to those having ordinary skill in the art.

III Methods of Producing Acrylic Acid, Metal Acrylate, or Mixtures Thereof

A method of dehydrating lactate salt to acrylic acid, acrylate salt, or mixtures thereof is provided. The lactate salt comprises a lactate anion and cation. The cation of the lactate salt can be selected from the group consisting of inorganic, organic, monoatomic, polyatomic, monovalent, polyvalent, and mixtures thereof.

Non-limiting examples of cations of the lactate salt are metallic cations, organo-metallic cations, ammonium, substituted ammonium, and other cations known by those skilled in the art. Non-limiting examples of monovalent cations of the lactate salt are $Li^+$, $Na^+$, $Rb^+$, $Cs^+$, $Ag^+$, $Rb^+$, $Tl^+$, and mixtures thereof. The polyvalent cation of the lactate salt can be selected from the group consisting of divalent cations, trivalent cations, tetravalent cations, pentavalent cations, and mixtures thereof. Non-limiting examples of polyvalent cations of the lactate salt are cations of the alkaline earth metals (i.e., Be, Mg, Ca, Sr, Ba, and Ra), transition metals (e.g. Y, Ti, Zr, V, Nb, Cr, Mo, Mn, Re, Fe, Ru, Co, Rh, Ni, Pd, Pt, Cu, Ag, and Au), poor metals (e.g. Zn, Ga, Si, Ge, B, Al, In, Sb, Sn, Bi, and Pb), and lanthanides (e.g. La and Ce). In one embodiment, the polyvalent cation is selected from the group consisting of $Be^{2+}$, $Mg^{2+}$, $Ca^{2+}$, $Sr^{2+}$, $Ba^{2+}$, $Mn^{2+}$, $Fe^{2+}$, $Co^{2+}$, $Ni^{2+}$, $Cu^{2+}$, $Zn^{2+}$, $Cd^{2+}$, $Sn^{2+}$, $Pb^{2+}$, $Ti^{3+}$, $Cr^{3+}$, $Mn^{3+}$, $Fe^{3+}$, $Al^{3+}$, $Ga^{3+}$, $Y^{3+}$, $In^{3+}$, $Sb^{3+}$, $Bi^{3+}$, $Er^{3+}$, $Si^{4+}$, $Ti^{4+}$, $V^{4+}$, $Ge^{4+}$, $Mo^{4+}$, $Pt^{4+}$, $V^{5+}$, $Nb^{5+}$, $Sb^{5+}$, and mixtures thereof. In another embodiment, the polyvalent cation is selected from the group consisting of $Mg^{2+}$, $Ca^{2+}$, $Sr^{2+}$, $Ba^{2+}$, $Mn^{2+}$, $Mn^{3+}$, $Al^{3+}$, $Y^{3+}$, $Er^{3+}$, and mixtures thereof; in yet another embodiment, the polyvalent cation is selected from the group consisting of $Ca^{2+}$, $Ba^{2+}$, $Mn^{2+}$, and mixtures thereof; and in even yet another embodiment, the polyvalent cation is $Ba^{2+}$. Non limiting examples of substituted ammonium and other cations are isopropylammonium, ethylenediammonium, sacrosinium, L-histidinium, glycinium, and 4-aminopyridinium.

In one embodiment, the cation of the lactate salt is a metallic cation, and the lactate salt is a metal lactate. In another embodiment, the metal in the metal lactate is selected from the group consisting of lithium, sodium, potassium, cesium, magnesium, calcium, strontium, and barium. In yet another embodiment, the metal in the metal lactate is selected from the group consisting of magnesium, calcium, strontium, and barium.

In one embodiment, the lactate salt is produced by contacting lactic acid, lactic acid derivates, or mixtures thereof, with a base. Non-limiting examples of base are hydroxide, salt of oxoanion, and salt of heteropolyanion. Non-limited examples of salt of oxoanion are phosphate, condensed phosphate, phosphate adduct, arsenate, condensed arsenate, nitrate, sulfate, borate, carbonate, chromate, vanadate, niobate, tantalate, selenate, and other monomeric oxoanion or polyoxoanion that may be apparent to those having ordinary skill in the art. Non-limiting examples of a salt of heteropolyanion are heteropolyphosphate, such as arsenatophosphate, phosphoaluminate, phosphoborate, phosphochromate, phosphomolybdate, phosphosilicate, phosphosulfate, phosphotungstate, and others that may be apparent to those having ordinary skill in the art. Non-limiting examples of phosphate adducts are adducts of phosphate anions with telluric acid, halides, borates, carbonates, nitrates, sulfates, chromates, silicates, oxalates, mixtures thereof, or others that may be apparent to those having ordinary skill in the art. In one embodiment, the production of the lactate salt from lactic acid, lactic acid derivates, or mixtures thereof and the dehydration of the lactate salt are performed in different reactors. In another embodiment of the present invention, the production of the lactate salt from lactic acid, lactic acid derivates, or mixtures thereof and the dehydration of the lactate salt are performed in the same reactor.

Acrylate salts can be salts of acrylic acid, salts of acrylic acid oligomers, or mixtures thereof. In one embodiment, the acrylate salt is metal acrylate. Metal acrylates can be metal salts of acrylic acid, metal salts of acrylic acid oligomers, or mixtures thereof. In another embodiment, the metal in the metal acrylate is selected from the group consisting of lithium, sodium, potassium, cesium, magnesium, calcium, strontium, and barium. In yet another embodiment, the metal in the metal acrylate is selected from the group consisting of sodium, potassium, and calcium.

In one embodiment, a method of making acrylic acid, acrylate salt, or mixtures thereof is provided. The method includes dehydrating a lactate salt by contacting a stream comprising the lactate salt with an acid-base bifunctional catalyst comprising an acidic site and a basic site, and wherein the acidic site is a Brønsted acid with a $pK_a$ about the $pK_a$ of lactic acid to about the plc of $KH_2PO_4$.

In one embodiment, the stream comprises a diluent. Non-limiting examples of the diluent are water, methanol, ethanol, acetone, C3 to C8 linear and branched alcohols, C5 to C8 linear and branched alkanes, ethyl acetate, non-volatile ethers (including diphenyl ether), and mixtures thereof. In another embodiment, the diluent comprises water.

In one embodiment, the stream comprises about 2 wt % to about 95 wt % lactate salt, based on the total weight of the stream. In another embodiment, the steam comprises about 5 wt % to about 50 wt % lactate salt, based on the total weight of the stream. In yet another embodiment, the stream comprises about 10 wt % to about 25 wt % lactate salt, based on the total weight of the stream. In one embodiment, the stream comprises about 20 wt % lactate salt, based on the total weight of the stream. In another embodiment, the stream comprises an aqueous solution of lactate salt.

In one embodiment, the temperature at which the stream comprising lactate salt contacts the acid-base bifunctional catalyst is less than about 700° C. In another embodiment, the temperature at which the stream comprising lactate salt contacts the acid-base bifunctional catalyst is less than 500° C. In yet another embodiment, the temperature at which the stream comprising lactate salt contacts the acid-base bifunctional catalyst is about 100° C. to about 500° C. In even yet another embodiment, the temperature at which the stream comprising lactate salt contacts the acid-base bifunctional catalyst is about 250° C. to about 450° C.

In one embodiment, the contacting of the stream with the acid-base bifunctional catalyst is performed with a residence time of about 0.1 s to about 1 day. In another embodiment, the contacting of the stream with the acid-base bifunctional catalyst is performed with a residence time of about 1 s to about 1 h. In yet another embodiment, the contacting of the stream with the acid-base bifunctional catalyst is performed with a residence time of about 2 s to about 30 min.

The stream comprising lactate salt contacts the acid-base bifunctional catalyst at a pressure ranging from less than atmospheric (vacuum) to much higher than atmospheric. In one embodiment, the stream comprising lactate salt contacts the acid-base bifunctional catalyst at a pressure of about 1 bar to about 400 bar. In another embodiment, the stream comprising lactate salt contacts the acid-base bifunctional catalyst at a pressure of about 5 bar to about 200 bar. In yet another embodiment, the stream comprising lactate salt contacts the acid-base bifunctional catalyst at a pressure of about 10 bar to about 100 bar. In even yet another embodiment, the stream comprising lactate salt contacts the acid-base bifunctional catalyst at a pressure less than about 25 bar.

The method of making acrylic acid, acrylate salt, or mixtures thereof can take place in various modes, such as, continuous, semi-continuous, or batch. Non-limiting examples of reactors where the method of making acrylic acid, acrylate salt, or mixtures thereof can be carried out are continuous stirred tank reactors (CSTR), fixed bed reactors, fluidized bed reactors, and trickle bed reactors. The reactors can be made with a single material or a composite material that has a different interior surface than exterior surface. In one embodiment, the interior surface of the reactor comprises material with less than 0.1% of Group 8 to 11 transition metals. In another embodiment, the interior surface of the reactor comprises material with less than 0.01% of Group 8 to 11 transition metals. In yet another embodiment, the interior surface of the reactor comprises a passivated material. In one embodiment, the interior surface of the reactor comprises material selected from the group consisting of quartz, borosilicate glass, silicon, hastelloy, inconel, manufactured sapphire, stainless steel, titanium, zirconium, tantalum, and mixtures thereof. In another embodiment, the interior surface of the reactor comprises a material selected from the group consisting of quartz or borosilicate glass. In yet another embodiment, the interior surface of the reactor comprises borosilicate glass. In even yet another embodiment, the interior surface of the reactor comprises stainless steel.

In one embodiment, the method includes contacting the acid-base bifunctional catalyst with a stream comprising lactate salt under conditions sufficient to produce acrylic acid, metal acrylate, or mixtures thereof in a yield of at least 50 mol %. In another embodiment, the method includes contacting the acid-base bifunctional catalyst with a steam comprising lactate salt under conditions sufficient to produce acrylic acid, metal acrylate, or mixtures thereof in a yield of at least about 70 mol %. In yet another embodiment, the method includes contacting the acid-base bifunctional catalyst with a stream comprising lactate salt under conditions sufficient to produce acrylic acid, metal acrylate, or mixtures thereof in a yield of at least about 80 mol %.

In one embodiment, the method to produce acrylic acid, acrylate salt, or mixtures thereof has a selectivity for acrylic acid, metal acrylate, or mixtures thereof of at least about 50 mol %. In another embodiment, the method to produce acrylic acid, acrylate salt, or mixtures thereof has a selectivity for acrylic acid, acrylate salt, or mixtures thereof of at least about 70 mol %. In yet another embodiment, the method to produce acrylic acid, acrylate salt, or mixtures thereof has a selectivity for acrylic acid, acrylate salt, or mixtures thereof of at least about 80 mol %.

In one embodiment, the method to produce acrylic acid, acrylate salt, or mixtures thereof has a selectivity for propanoic acid (as an impurity) of less than about 5 mol %. In another embodiment, the method to produce acrylic acid, acrylate salt, or mixtures thereof has a selectivity for propanoic acid of less than about 1 mol %.

In one embodiment, the method to produce acrylic acid, acrylate salt, or mixtures thereof has a conversion of lactate salt of at least about 50 mol %. In another embodiment, the method to produce acrylic acid, acrylate salt, or mixtures thereof has a conversion of lactate salt of at least about 80 mol %.

Among the benefits attainable by the foregoing embodiments is the low yield of side products. In one embodiment, the conditions are sufficient to produce each of acetic acid, pyruvic acid, 1,2-propanediol, and 2,3-pentanedione in a yield of less than about 2 mol % from lactate salt present in the stream. In another embodiment, the conditions are sufficient to produce each of acetic acid, pyruvic acid, 1,2-propanediol, and 2,3-pentanedione in a yield of less than about 0.5 mol %, from lactate salt present in the stream. In one embodiment, the conditions are sufficient to produce acetaldehyde in a yield of less than about 8 mol % from lactate salt present in the stream. In another embodiment, the conditions are sufficient to produce acetaldehyde in a yield of less than about 4 mol % from lactate salt present in the stream. In yet another embodiment, the conditions are sufficient to produce acetaldehyde in a yield of less than about 3 mol %, from lactate salt present in the stream.

A method of making acrylic acid, sodium acrylate, or mixtures thereof is provided. In one embodiment of the present invention, the method includes contacting: (a) a stream comprising: sodium lactate, and a solvent, with (b) an acid-base bifunctional catalyst comprising an acidic site and a basic site, wherein the acidic site is a Brønsted acid with a $pK_a$ of about 4.5 to about 6.2, and wherein, the contacting of the stream with the acid-base bifunctional catalyst is performed at a temperature less than about 400° C., and at a residence time less than about 1 day, whereby acrylic acid, sodium acrylate, or mixtures thereof are produced as a result of the stream contacting the acid-base bifunctional catalyst. In another embodiment, the solvent comprises water. In yet another embodiment, the acid-base bifunctional catalyst comprises $KH_2PO_4$.

The dimensions and values disclosed herein are not to be understood as being strictly limited to the exact numerical values recited. Instead, unless otherwise specified, each such dimension is intended to mean both the recited value and a functionally equivalent range surrounding that value. For example, a dimension disclosed as "40 mm" is intended to mean "about 40 mm."

Every document cited herein, including any cross referenced or related patent or patent application, is hereby incorporated herein by reference in its entirety unless expressly excluded or otherwise limited. The citation of any document is not an admission that it is prior art with respect to any invention disclosed or claimed herein or that it alone, or in any combination with any other reference or references, teaches, suggests or discloses any such invention. Further, to the extent that any meaning or definition of a term in this document conflicts with any meaning or definition of the same term in a document incorporated by reference, the meaning or definition assigned to that term in this document shall govern.

While particular embodiments of the present invention have been illustrated and described, it would be obvious to those skilled in the art that various other changes and modifications can be made without departing from the spirit and scope of the invention. It is therefore intended to cover in the appended claims all such changes and modifications that are within the scope of the present invention.

What is claimed is:

1. A method of making acrylic acid, metal acrylate, or mixtures thereof comprising dehydrating a metal lactate by contacting a stream comprising said metal lactate with a $KH_2PO_4$ catalyst comprising an acidic site and a basic site, and wherein said acidic site is a Brønsted acid with a $pK_a$ of about 4 to about 7, wherein the stream comprises a diluent selected from the group consisting of acetone, C3 to C8 linear and branched alcohols, C5 to C8 linear and branched alkanes, ethyl acetate, non-volatile ethers (including diphenyl ether), and mixtures thereof.

2. The method of claim 1, wherein said $pK_a$ is about 4.5 to about 6.2.

3. The method of claim 2, wherein said $pK_a$ is about 5.3.

4. The method of claim 1, wherein said catalyst is generated from a polyphosphate by hydrolysis.

5. The method of claim 1, wherein said catalyst includes an inert support that is constructed of a material selected from the group consisting of silicates, aluminates, zirconates, carbons, metal oxides, and mixtures thereof.

6. The method of claim 1, wherein the metal in said metal lactate is selected from the group consisting of lithium, sodium, potassium, cesium, magnesium, calcium, strontium, and barium.

7. The method of claim 1, wherein said stream contacts said catalyst at a temperature less than about 700° C.

8. The method of claim 7, wherein said temperature is about 250° C. to about 450° C.

9. The method of claim 1, wherein said contacting of said stream with said catalyst is performed with a residence time of about 0.1 s to about 1 day.

10. The method of claim 9, wherein said residence time is about 1 s to about 1 h.

11. The method of claim 1, wherein said stream contacts said catalyst at a pressure of about 5 bar to about 100 bar.

12. The method of claim 11, wherein said pressure is less than about 25 bar.

13. The method of claim 1, wherein said method has a selectivity for acrylic acid, metal acrylate, and mixtures thereof of at least about 80 mol %.

14. The method of claim 1, wherein said method has a selectivity for propionic acid of less than about 1 mol %.

15. The method of claim 1, wherein said method has a conversion of metal lactate of at least about 80 mol %.

16. A method of making acrylic acid, sodium acrylate, or mixtures thereof comprising contacting:
   a. a stream comprising:
      i. sodium lactate, and
      ii. a solvent, with
   b. a $KH_2PO_4$ catalyst comprising an acidic site and a basic site, wherein said acidic site is a Brønsted acid with a $pK_a$ of about 4.5 to about 6.2, and wherein, said contacting of said stream with said acid-base bifunctional catalyst is performed at a temperature about 250° C. to about 450° C., and at a residence time less than about 1 day, whereby acrylic acid, sodium acrylate, or mixtures thereof are produced as a result of said stream contacting said acid-base bifunctional catalyst.

17. The method of claim 16, wherein said solvent comprises water.

* * * * *